United States Patent
Fritsch et al.

(10) Patent No.: US 6,785,929 B2
(45) Date of Patent: Sep. 7, 2004

(54) ELECTRIC TOOTHBRUSH (75) Inventors: Thomas Fritsch, Eppstein (DE); Peter Hilfinger, Bad Homburg (DE)

(73) Assignee: Braun GmbH (DE)

(*) Notice: Subject to any disclaimer, the term of this patent is extended or adjusted under 35 U.S.C. 154(b) by 0 days.

(21) Appl. No.: 10/319,114

(22) Filed: Dec. 12, 2002

(65) Prior Publication Data

US 2003/0126698 A1 Jul. 10, 2003

Related U.S. Application Data (63) Continuation of application No. PCT/EP01/07615, filed on Jul. 4, 2001.

(30) Foreign Application Priority Data

Jul. 19, 2000 (DE) .......................... 100 34 957

(51) Int. Cl.[7] .............................. A46B 13/02
(52) U.S. Cl. .................. 15/167.1; 15/22.1; 15/201
(58) Field of Search ................ 15/167.1, 22.1, 15/22.2

(56) References Cited

U.S. PATENT DOCUMENTS

| | | | |
|---|---|---|---|
| 5,184,368 A | * 2/1993 | Holland | 15/167.1 |
| 5,546,626 A | 8/1996 | Chung | |
| 5,836,030 A | 11/1998 | Hazeu et al. | |
| 5,956,797 A | * 9/1999 | Wilson | 15/167.1 |
| 6,463,615 B1 | * 10/2002 | Gruber et al. | 15/22.1 |

FOREIGN PATENT DOCUMENTS

| | | |
|---|---|---|
| DE | 36 18 823 C2 | 6/1995 |
| DE | 43 09 035 C2 | 4/1999 |
| EP | 0 322 562 A1 | 11/1988 |
| WO | WO 97/24079 | 7/1997 |
| WO | WO 99/56660 | 11/1999 |
| WO | WO 01/32095 | 5/2001 |

* cited by examiner

Primary Examiner—Robert J. Warden, Sr.
Assistant Examiner—Shay L Balsis
(74) Attorney, Agent, or Firm—Fish & Richardson P.C.

(57) ABSTRACT

An electric toothbrush is provided, which includes a first bristle part that can be made to execute a first, continuously repeating movement. An additional bristle part, connected to the first bristle part, can be made to execute a second, continuously repeating movement, which differs from the first movement of the first bristle part.

8 Claims, 6 Drawing Sheets

ELECTRIC TOOTHBRUSH

CROSS REFERENCE TO RELATED APPLICATION

This is a continuation of PCT application serial no. PCT/EP01/07615, filed Jul. 4, 2001, which claims priority from German application serial number 10034957.9, filed Jul. 19, 2000.

TECHNICAL FIELD

This invention relates to electric toothbrushes.

BACKGROUND

Electric toothbrushes are known in general (DE 43 09 035 C2) and are commercially available (WO 97/24079). Electric toothbrushes may include a bristle part which together with a carrier tube, is pivoted back and forth about the longitudinal axis of the carrier tube and thus about an axis which runs perpendicularly to the clusters of bristles. Other electric toothbrushes include a bristle part that is made to execute a rotary movement, or an alternating pivoting movement or oscillating rotation, about an axis which runs parallel to the clusters of bristles. The essential factor is for a continuously repeating, in particular periodic movement of the bristle part to be provided.

If a user uses the electric toothbrush for teeth-cleaning purposes, then the free ends of the clusters of bristles are positioned on the surfaces of the teeth. The continuously repeating movement of the bristle part results in the clusters of bristles subjecting the surfaces of the teeth to a cleaning action.

SUMMARY

One object of the invention is to provide an electric toothbrush which provides good cleaning, in particular in interdental regions, and is of straightforward construction.

In one aspect, the invention features an electric toothbrush having a first bristle part, which can be made to execute a first movement, and an additional bristle part which is connected to the first bristle part and which can be made to execute a second movement, which differs from the first movement of the first bristle part. The second movement of the additional bristle part can be brought about by the first movement of the first bristle part, by way of a resonance effect.

In some implementations, the second movement of the additional bristle part allows the interdental regions to be cleaned in a specific manner during the tooth-cleaning operation. This specific targeting of the interdental regions is made possible in that the second movement of the additional bristle part differs from the first movement of the bristle part. It is thus possible for the surfaces of the teeth to be cleaned, as has been the case hitherto, with the aid of the bristles or clusters of bristles of the first bristle part, while the interdental regions can be cleaned independently by means of the second movement of the additional bristle part. The additional bristle part may be designed, and coordinated with the continuously repeating movement of the first bristle part, so as to produce the resonance effect. The two differing movements of the first bristle part and of the additional bristle part achieve, overall, improved cleaning of the teeth and, in particular, of the interdental regions. In addition, the toothbrush is of straightforward design.

In some implementations, the additional bristle part is not connected rigidly to the first bristle part. By virtue of the first bristle part and the additional bristle part being connected in a flexible and/or elastic manner instead, the invention achieves the situation where the bristle part and the additional bristle part execute movements which differ from one another and can be used for cleaning the surfaces of the teeth and the interdental regions.

The additional bristle part may be connected to the first bristle part via a spring element. It may facilitate production, in this case, if the first bristle part, the additional bristle part and the spring element are formed in one piece.

This makes it possible, according to the invention, to achieve the desired flexible connection between the first bristle part and the additional bristle part without high design-related outlay. The single-piece configuration, in particular, realizes the invention in a particularly straightforward and cost-effective manner.

The second movement of the additional bristle part may be dependent on the first movement of the first bristle part, insofar as the second movement is brought about by the first movement. At the same time, however, the first movement, on account of the flexible connection between the first bristle part and the additional bristle part, differs from the second movement.

In the case of an advantageous development of the invention, the additional bristle part can be made to execute a continuously pivoting or periodic movement by means of the resonance effect.

The second movement of the additional bristle part may be coupled to the first movement of the first bristle part via a resonance effect. The additional bristle part is made to execute its second movement by the first movement of the first bristle part, by way of a resonance effect. The invention utilizes the abovementioned resonance effect in order to cause the additional bristle part to execute the second movement. This constitutes a particularly straightforward and thus cost-effective method of producing the two differing movements of the first bristle part and additional bristle part according to the invention.

Preferably, the second movement of the additional bristle part has an amplitude that is greater than that of the first movement of the first bristle part. This may be achieved by the abovementioned resonance effect being exploited as fully as possible. It is also possible for the frequency and/or the time dependence and/or the movement direction of the second movement to differ from the first movement.

In the case of a further configuration of the invention, the additional bristle part is provided with clusters of bristles, and the second movement of the additional bristle part takes place approximately or essentially in the bristle direction. This provides the significant advantage that the second movement of the cluster of bristles of the additional bristle part is oriented specifically in the direction of the tooth surface. If the clusters of bristles of the additional bristle part butt against a surface of a tooth, then the second movement, directed in relation to the tooth surface, of said clusters of bristles is damped. If the clusters of bristles of the additional bristle part, however, are located in the region of a space between the tooth, that is to say in an interdental region, then the clusters of bristles of the additional bristle part can execute their directed second movement in an essentially undamped manner. This results in the clusters of bristles of the additional bristle part penetrating specifically and deeply into the interdental region and cleaning the adjacent tooth surfaces there. This constitutes a considerable improvement in cleaning the surface between the teeth.

It is expedient here if the additional bristle part is guided such that it can move essentially in the bristle direction. This straightforwardly achieves the specifically directed movement of the clusters of bristles of the additional bristle part and the advantages which are associated therewith.

The invention is also realized by a bristle carrier for an electric toothbrush, which is provided with a bristle part which can be made to execute a first, continuously repeating movement. Also provided in this case is an additional bristle part which is connected to the bristle part and which can be made to execute a second, continuously repeating movement, which differs from the first movement of the bristle part, use being made of a resonance effect.

Further features, possible applications and advantages of the invention can be gathered from the following description of exemplary embodiments of the invention, which are illustrated in the figures.

DETAILED DESCRIPTION

An electrically driven toothbrush has a handle part and a bristle carrier. The bristle carrier may be designed such that it can be plugged onto the handle part.

The bristle carrier has a carrier tube and a bristle part. The bristle part is provided with a bristle arrangement which has a multiplicity of bristles, which are arranged in clusters of bristles. The bristles project approximately at right angles from the bristle part and thus define a bristle direction.

Accommodated in the handle part, inter alia, is a drive, by means of which the bristle carrier as a whole and/or the bristle part as a whole and/or part of the bristle arrangement and/or individual clusters of bristles can be made to execute a movement.

The drive may be any type of drive, that is to say a rotary drive, an oscillating drive, an alternating drive, an eccentric drive, an unbalance-generating drive and/or the like. The drive may be realized in the form of an electric motor or of some other kind of motor. The movement produced by the drive may be transmitted to the bristle carrier and/or the bristle part and/or the clusters of bristles in any desired manner, for example by means of a drive spindle or the like.

The drive can cause the bristle carrier and/or the bristle part and/or parts of the bristle arrangement and/or the clusters of bristles to execute any type of movement. For example, the bristle carrier and/or the bristle part and/or the bristle arrangement and/or part thereof and/or the clusters of bristles may be made to execute an alternating movement about an axis which is oriented parallel, or at right angles or at any other angle, to the bristle direction.

The drive causes the bristle carrier and/or the bristle part and/or the bristle arrangement and/or parts of the bristle arrangement and/or the clusters of bristles to execute a continuously repeating movement which has a certain frequency. The direction of the movement here is not important. It is also possible for the movement to be completely undirected. This movement described above is also referred to as the first movement.

Figure 1:
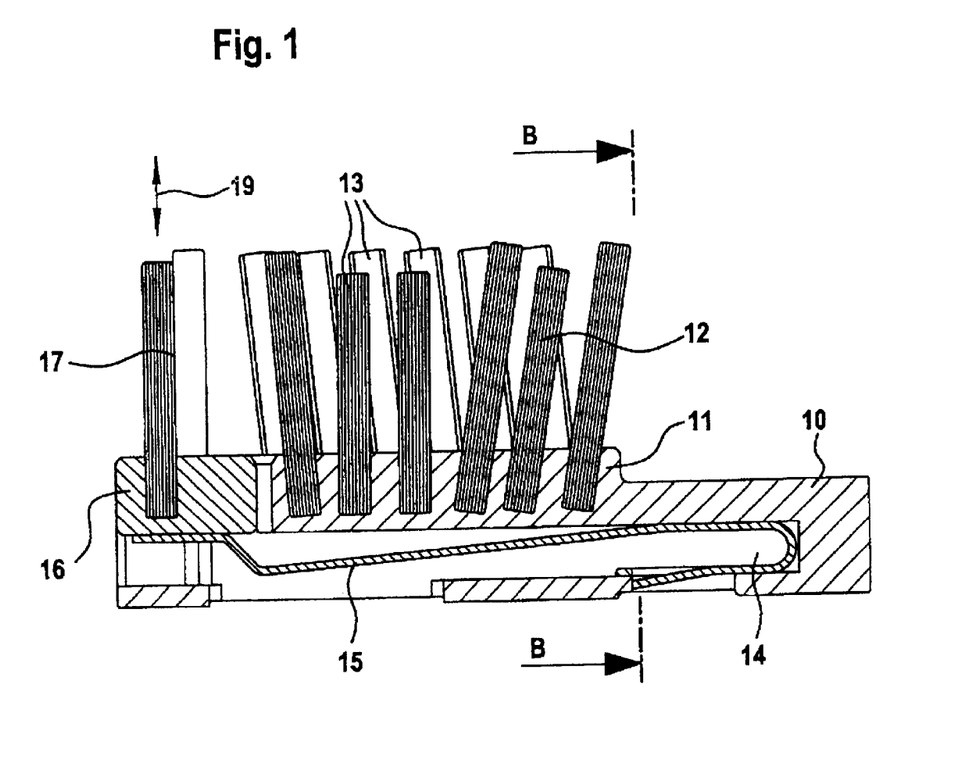
FIG. 1 shows a first exemplary embodiment of an electrically driven toothbrush according to the invention in a schematic longitudinal section in a plane parallel to the bristle direction.

FIG. 1 illustrates a first exemplary embodiment of an electrically driven toothbrush which has a carrier tube 10 with a first bristle part 11. Projecting from the bristle part 11 is a first bristle arrangement 12, which has a multiplicity of clusters of bristles 13. In FIG. 1, the carrier tube 10 is made to execute an alternating pivoting movement about its longitudinal axis by a drive.

A cutout 14 is provided in the region of the carrier tube 10, a spring element 15 being pushed into said cutout and clamped firmly therein. The spring element 15 is arranged in the longitudinal direction of the carrier tube 10 and extends beyond the region of the bristle part 11. The spring element 15 may be, for example, a leaf spring.

Provided at that end of the bristle part 11 directed away from the carrier tube 10 is an additional bristle part 16, from which there projects an additional bristle arrangement 17 with a plurality of clusters of bristles. The additional bristle arrangement 17 supplements the bristle arrangement 12 formed by the bristle part 11. In a rest state in particular, the free ends of the clusters of bristles of the bristle arrangement 12 and of the additional bristle arrangement 17 form an approximately planar surface.

The additional bristle part 16 is firmly connected to the free end of the spring element 15. This is the only connection of the additional bristle part 16 to the bristle part 11 and the carrier tube 10. Rather than being connected rigidly, the additional bristle part 16 is thus only connected in a flexible manner, via the spring element 15, to the bristle part 11 and the carrier tube 10.

Figure 1A:
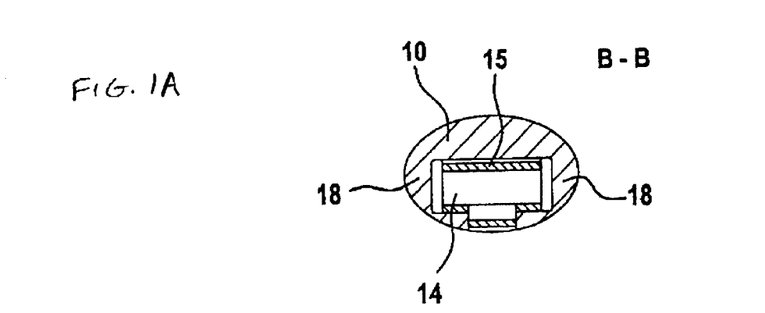
FIG. 1A is a schematic cross section taken along plane B—B in FIG. 1.

Referring to FIG. 1A, the spring element 15 and/or the additional bristle part 16 is guided, for example, by side walls 18 of the carrier tube 10 such that the additional bristle part 16 can only move in the bristle direction. The bristle direction, and thus the movement direction of the additional bristle part 16, is indicated by an arrow 19 in FIG. 1.

The dimensions of the spring element 15 of the additional bristle part 16 and the spring constant of the spring element 15 are such that, when the electrically driven toothbrush is switched on, a resonance effect is produced. This means that, in a switched-on state, the additional bristle part 16 is made to execute a resonance movement on the spring element 15, the frequency of the resonance movement corresponding approximately to a resonant frequency of the electric drive.

By virtue of the resonance effect and the resulting resonance movement of the additional bristle part 16, and on account of the guidance of the additional bristle part 16 in the bristle direction, the additional bristle arrangement 17 is made to move in the direction of the arrow 19. This means that the additional bristle arrangement 17 is continuously made to execute a directed movement in the bristle direction. This movement is thus directed and is also referred to as the second movement.

The movement of the additional bristle arrangement 17 here may have an amplitude that is greater than that of the movement of the first bristle arrangement 12. This depends on the spring element 15 and the additional bristle part 16 being coordinated with a resonant frequency of the electric drive.

If a user positions the electrically driven toothbrush with the free ends of the bristle arrangement 12 and the additional bristle arrangement 17 on the surface of the teeth for teeth-cleaning purposes, this results in damping of the resonance-effect-induced movement of the additional bristle arrangement 17 in the bristle direction. However, as soon as the clusters of bristles of the additional bristle arrangement 17 pass into the region of a space between the teeth, that is to say into an interdental region, there is no longer any damping of the above-mentioned movement of the additional bristle arrangement 17 in the bristle direction by the surface of the teeth.

Instead, on account of the resonance-effect-induced movement in the direction of the arrow 19, the clusters of bristles of the additional bristle arrangement 17 are moved right into the space between the teeth. In an interdental region, the clusters of bristles of the additional bristle arrangement 17 execute a picking movement precisely in the direction of the space between the teeth. The cleaning of the space between the teeth is improved in this way.

Figure 2:
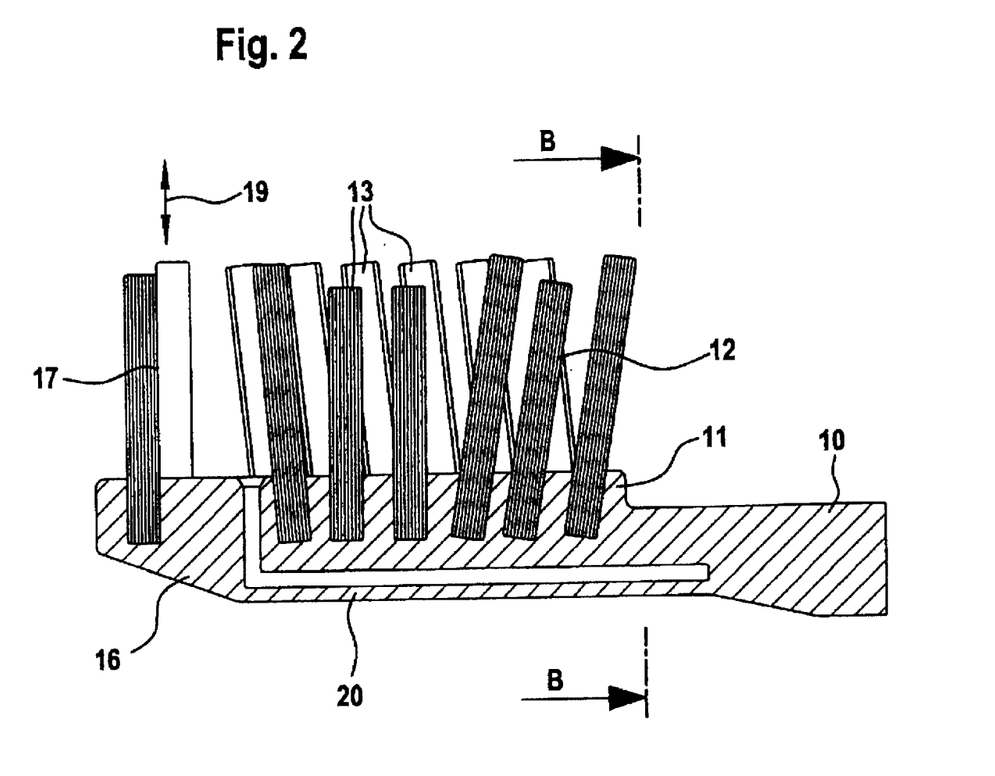
FIG. 2 shows a second exemplary embodiment of an electrically driven toothbrush according to the invention in a schematic longitudinal section in a plane parallel to the bristle direction.
Figure 2A:
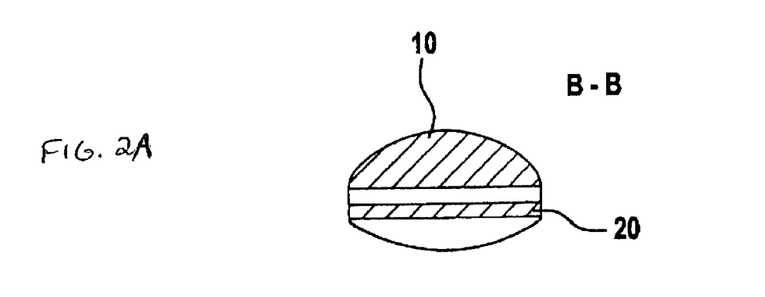
FIG. 2A is a schematic cross section taken along plane B—B in FIG. 2.

FIG. 2 illustrates a second exemplary embodiment of an electrically driven toothbrush, which largely corresponds to the first exemplary embodiment from FIG. 1. The same components are thus indicated by the same designations.

In contrast to FIG. 1, however, in the case of FIG. 2, the spring element is formed by a web 20, which does not constitute an additional component. The web 20 is connected integrally to the carrier tube 10 and the additional bristle part 16. By virtue of selecting an appropriate material for the web 20, in particular an appropriate plastic, and by virtue of corresponding adaptation of the dimensions, in particular of the thickness of the web 20, the web 20 may be assigned resilient properties which correspond to the resilient properties of the spring element from FIG. 1.

Specific guidance of the web 20 and/or the additional bristle part 16 is not necessary in the case of FIG. 2. This guidance is already achieved by the single-piece configuration of the web 20, the additional bristle part 16 and the carrier tube 10.

Figure 3:
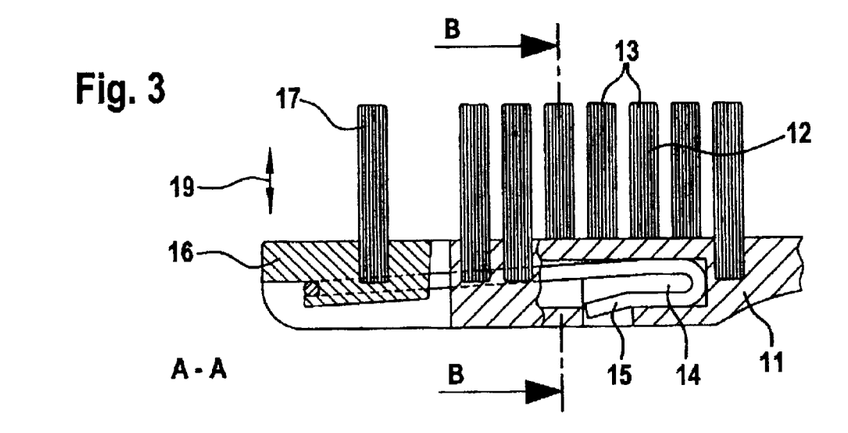
FIG. 3 shows a third exemplary embodiment of an electrically driven toothbrush according to the invention in a schematic longitudinal section in a plane oriented at right angles to the bristle direction.
Figure 3A:
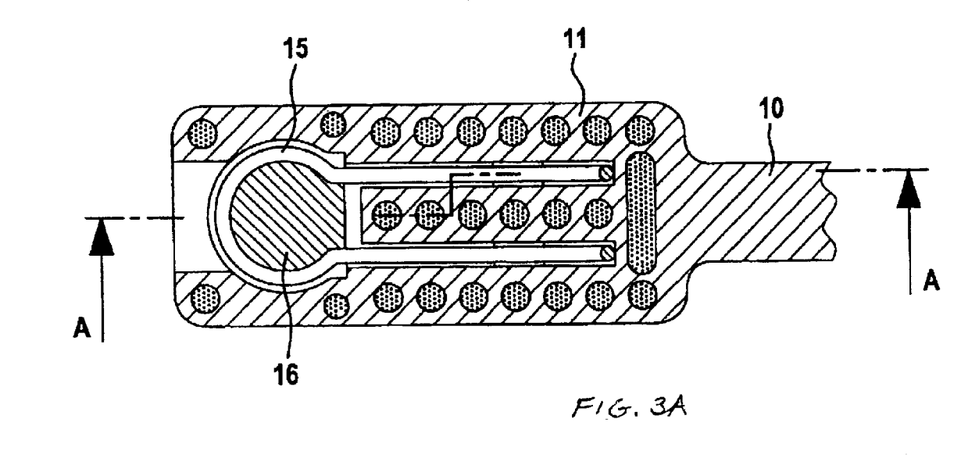
FIG. 3A is a schematic longitudinal section along taken along plane AA in FIG. 3.
Figure 3B:
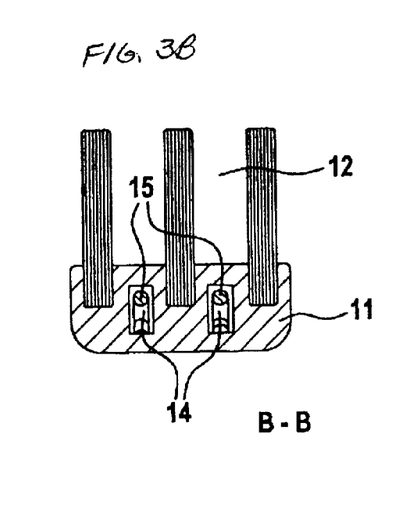
FIG. 3B is a schematic cross section taken along plane B—B in FIG. 3.

FIG. 3 illustrates a third exemplary embodiment of an electrically driven toothbrush, which largely corresponds to the first exemplary embodiment in FIG. 1. The same components are thus indicated by the same designations.

In contrast to FIG. 1, however, in the case of FIG. 3, the spring element is designed as a U-shaped wire spring. The two ends of the spring element 15 from FIG. 3 are clamped firmly in the cutout 14 of the carrier tube 10. In its arcuate region, the spring element 15 from FIG. 3 is connected to the additional bristle part 16.

The cutout 14 is continued, at least in part, as gap-like openings in the bristle part 11. The wire spring, which serves as spring element 15, is arranged within these openings. In comparison with FIG. 1, the movement of the spring element 15 from FIG. 3 is thus not limited by the bristle part 11. In the case of FIG. 3, the additional bristle part 16 may thus execute a large-amplitude movement.

Figures 4, 4A:
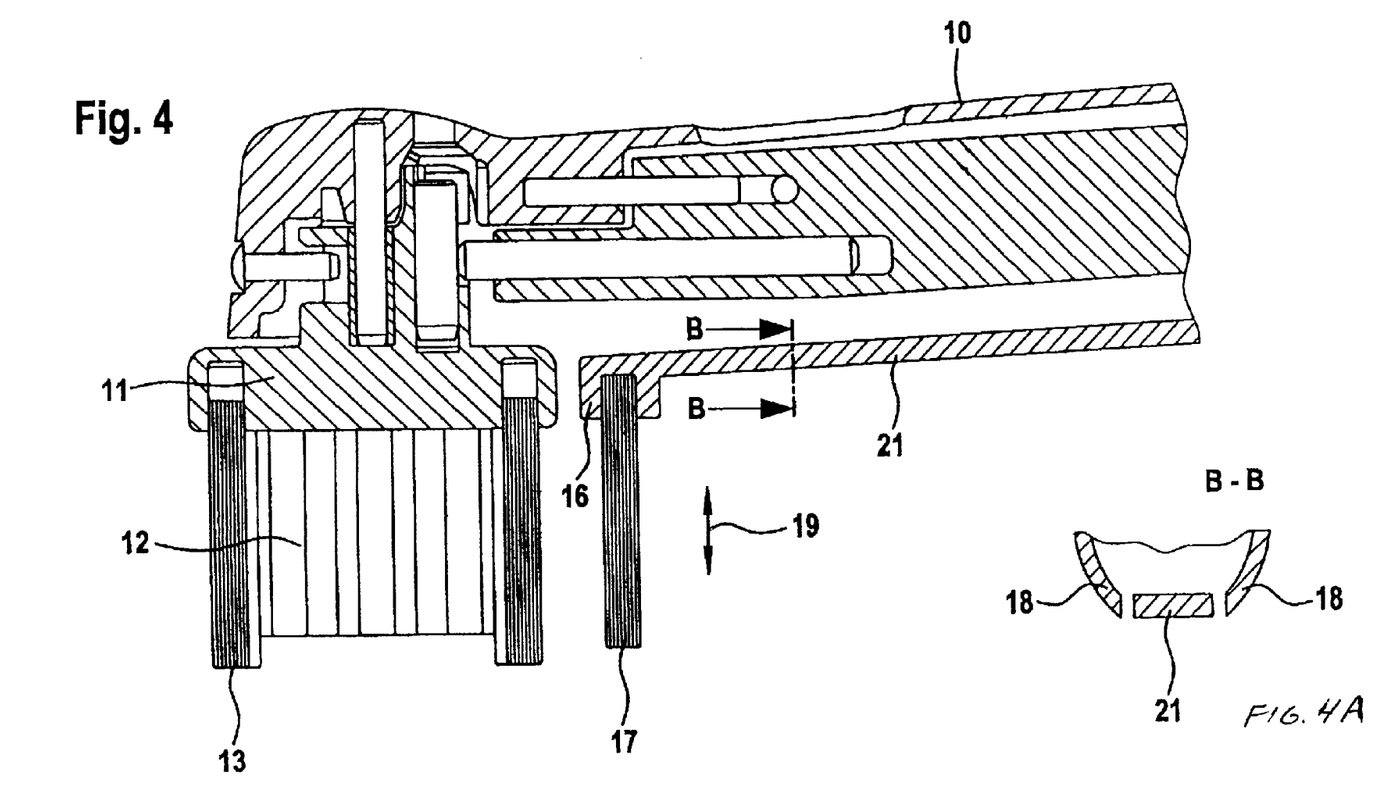
FIG. 4 shows a fourth exemplary embodiment of an electrically driven toothbrush according to the invention in a schematic longitudinal section in a plane parallel to the bristle direction.
FIG. 4A is a schematic cross section taken along plane B—B in FIG. 4.

FIG. 4 illustrates a fourth exemplary embodiment of an electrically driven toothbrush. The same components are indicated by the same designations.

In contrast to FIGS. 1 to 3, in the case of FIG. 4, the bristle part 11 is made to execute not just a pivoting movement which alternates in relation to the longitudinal axis of the carrier tube 10, but also, or only, a rotary or pivoting movement about an axis which is parallel to the bristle direction. This is achieved by a deflecting gear mechanism or the like, which is accommodated in the carrier tube 10.

In a manner similar to FIG. 2, FIG. 4 shows a web 21 connected integrally to the carrier tube 10. The free end of the web 21 then merges into the additional bristle part 16. As can be gathered, in particular, from the cross section B—B (FIG. 4A), the web 21 is guided by the side walls 18 of the carrier tube 10.

In the switched-on state, the additional bristle part 16, which is retained on the web 21, is made to execute a movement in the direction of the arrow 19, along with the additional bristle arrangement 17, on account of the resonance effect described. In the case of FIG. 4, the abovementioned resonance effect may be brought about by the alternating rotary or pivoting movement of the bristle part 1.

Figure 5:
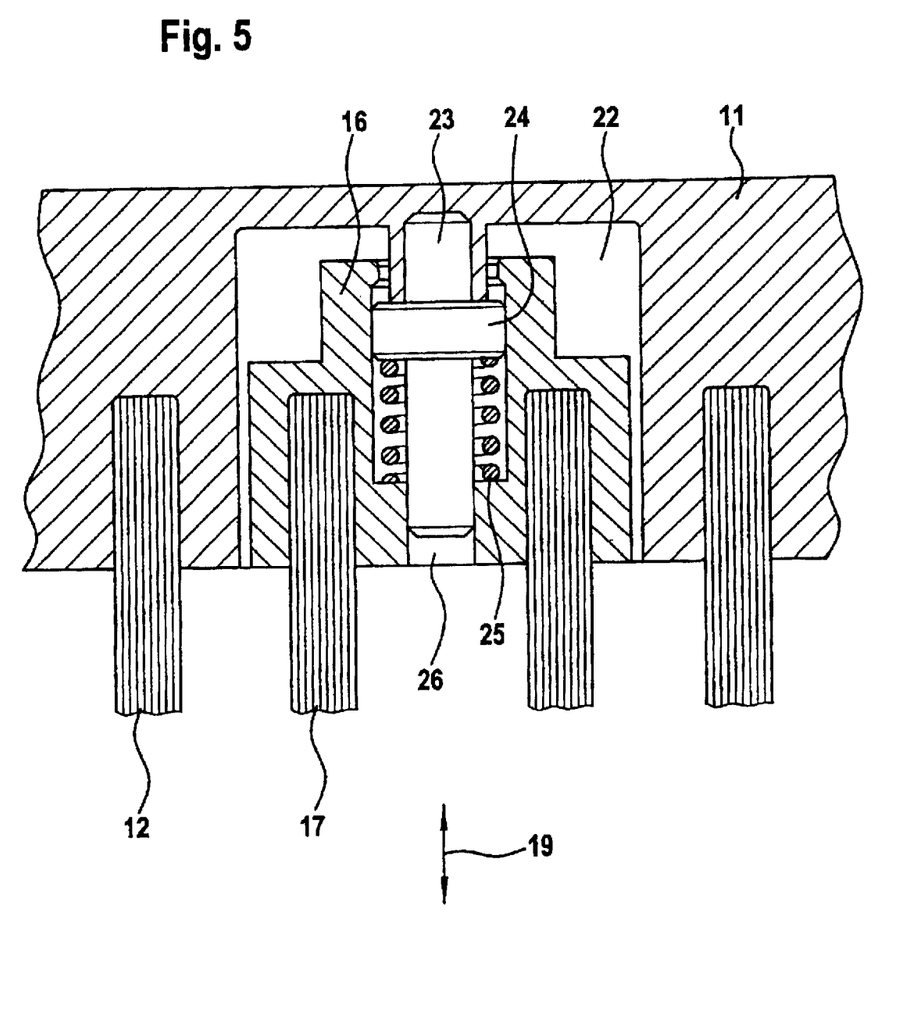
FIG. 5 shows a fifth exemplary embodiment of an electrically driven toothbrush according to the invention in a schematic longitudinal section in a plane parallel to the bristle direction.
Figure 6:
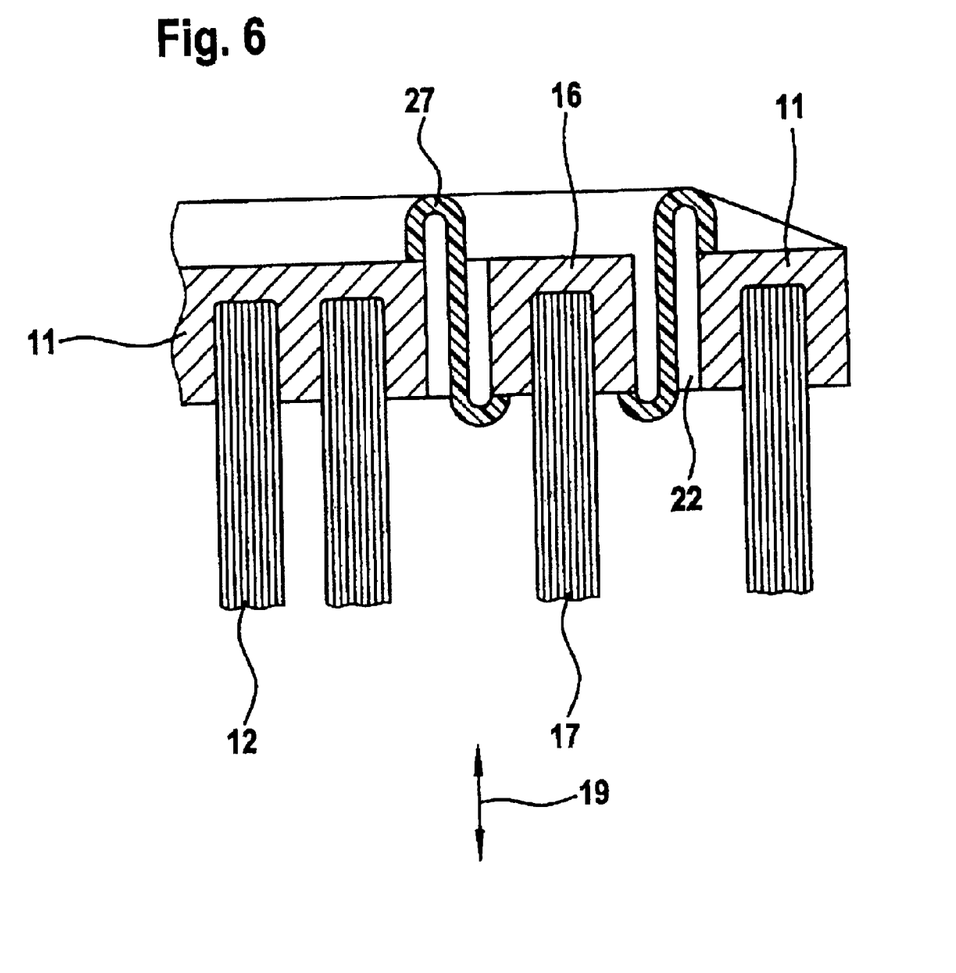
FIG. 6 shows a sixth exemplary embodiment of an electrically driven toothbrush according to the invention in a schematic longitudinal section in a plane parallel to the bristle direction.

FIGS. 5 and 6 illustrate two further exemplary embodiments of an electrically driven toothbrush. The two exemplary embodiments may be used as an alternative, or in addition, to the exemplary embodiments of FIGS. 1 to 4. The same components are thus indicated by the same designations.

In FIG. 5, the bristle part 11 is provided with a cutout 22, within which the additional bristle part 16 is arranged. The cutout 22 and the additional bristle part 16 are of cylindrical design and plugged one inside the other. Firmly connected to the bristle part 11 is a guide pin 23, which projects parallel to the arrow 19 in the direction of the additional bristle part 16. A ring 24, on which a spring element 25 is supported, is retained on the guide pin 23. The spring element 25, in FIG. 5, may be a helical spring. By means of its other end, the spring element 25 butts against the additional bristle part 16. The additional bristle part 16 further contains a bore 26, into which the guide pin 23 penetrates with sliding action.

When the electrically driven toothbrush is switched on, the additional bristle part 16 is made to execute a movement in the direction of the arrow 19 by way of the resonance effect described. The additional bristle part 16 is guided here by the guide pin 23. The resonance effect is produced on account of the spring element 25 taking effect between the additional bristle part 16 and the bristle part 11.

FIG. 6 largely corresponds to FIG. 5. In contrast to FIG. 5, however, in the case of FIG. 6, the bristle part 11 is connected to the additional bristle part 16 directly with the aid of a single-piece spring element 27. The spring element 27 may be, for example, a cylindrical component of which the free edges are connected to the bristle part 11 and the additional bristle part 16.

The spring element 27 may consist of an elastic material, for example of a plastic. The bristle part 11, the additional bristle part 16 and the spring element 27 may be produced in plastic as a multi-component injection molding.

A number of embodiments of the invention have been described. Nevertheless, it will be understood that various modifications may be made without departing from the spirit and scope of the invention.

What is claimed is:

1. An electric toothbrush comprising:
   a first bristle part, which can be made to execute a first movement, and
   an additional bristle part, connected to the first bristle part, which can be made to execute a second movement, which differs from the first movement of the first bristle part,
   wherein the second movement of the additional bristle part is brought about by the first movement of the first bristle part, by way of a resonance effect, and takes place in a bristle direction, and
   wherein the additional bristle part is guided such that the additional bristle part moves essentially only in the bristle direction.

2. A toothbrush according to claim 1, characterized in that the additional bristle part is not connected rigidly to the first bristle part.

3. A toothbrush according to claim 2, characterized in that the additional bristle part is connected to the first bristle part via a spring element.

4. A toothbrush according to claim 3, characterized in that the first bristle part, the additional bristle part, and the spring element are formed in one piece.

5. A toothbrush according to claim 1, characterized in that the additional bristle part and/or the first bristle part can be made to execute a continuously repeating movement.

6. A toothbrush according to claim 5, characterized in that the additional bristle part is designed, and coordinated with the continuously repeating movement of the first bristle part, so as to produce the resonance effect.

7. A toothbrush according to claim 1, characterized in that the second movement of the additional bristle part has an amplitude greater than that of the first movement of the first bristle part.

8. A bristle carrier for an electric toothbrush having a first bristle part, which can be made to execute a first, continuously repeating movement, and an additional bristle part which is connected to the first bristle part and which can be made to execute a second, continuously repeating movement, which differs from the first movement of the first bristle part, characterized in that the second movement of the additional bristle part can be brought about by the first movement of the first bristle part, by way of a resonance effect, and the second movement takes place in a bristle direction and the additional bristle part is guided such that the additional bristle part moves essentially only in the bristle direction.

* * * * *